US007700837B2

(12) United States Patent
Kim et al.

(10) Patent No.: US 7,700,837 B2
(45) Date of Patent: Apr. 20, 2010

(54) TRANSFORMED PLANT CELL EXPRESSING TANDEM REPEATS OF BETA-AMYLOID GENE AND PLANT PRODUCED BY THE SAME

(75) Inventors: Hyun Soon Kim, Daejeon (KR); Jung Won Youm, Daejeon (KR); Jae Heung Jeon, Daejeon (KR); Mi Sun Kim, Daejeon (KR); Inhee Mook, Seongnam-si (KR); Hyouk Joung, Daejeon (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 1190 days.

(21) Appl. No.: 10/545,882

(22) PCT Filed: Mar. 11, 2004

(86) PCT No.: PCT/KR2004/000501

§ 371 (c)(1),
(2), (4) Date: Aug. 17, 2005

(87) PCT Pub. No.: WO2004/083417

PCT Pub. Date: Sep. 30, 2004

(65) Prior Publication Data

US 2008/0213340 A1   Sep. 4, 2008

(30) Foreign Application Priority Data

Mar. 21, 2003   (KR) .................... 10-2003-0017766

(51) Int. Cl.
*A01H 5/00* (2006.01)
*C12N 15/82* (2006.01)

(52) U.S. Cl. .................. 800/295; 800/298; 800/288; 800/278

(58) Field of Classification Search ................ None
See application file for complete search history.

(56) References Cited

U.S. PATENT DOCUMENTS 4,956,282 A * 9/1990 Goodman et al. ....... 435/69.51

FOREIGN PATENT DOCUMENTS

WO   WO 98/21348   *   5/1998
WO   WO 03/015812   *   2/2003

OTHER PUBLICATIONS

Kim et al. Expression of human Beta-amyloid peptide in transgenic potato. (2003) Plant Science; vol. 165, pp. 1445-1451.*
Akama et al. Amyloid beta-peptide stimulates nitric oxide production in astrocytes through an NFkappaB-dependent mechanism. (1998) PNAS; vol. 95, pp. 5795-5800.*
Giddings, G. Transgenic plants as protein factories. (2001) Current Opinion in Biotechnology; vol. 12; pp. 450-454.*
Bacskai et al., "Imaging of amyloid-β deposits in brains of living mice permits direct observation of clearance of plaques with immunotherapy", Nature Medicine 2001 7:369-372.
Chen et al., "A learning deficit related to age and β-amyloid plaques in a mouse model of Alzheimer's disease", Nature 2000 408:975-979.
Chong et al., "Expression of the human milk protein β-casein in transgenic potato plants", Transgenic Research 1997 6:289-296.
Janus et al., "Aβ peptide immunization reduces behavioural impairment and plaques in a model of Alzheimer's disease", Nature 2000 408:979-985.
Sandhu et al., "Oral immunization of mice with transgenic tomato fruit expressing respiratory syncytial virus-F protein induces a systemic immune response", Transgenic Research 2000 9:127-135.
Schenk et al., "Immunization with amyloid-β attenuates Alzheimer-disease-like pathology in the PDAPP mouse", Nature 1999 400:173-177.

* cited by examiner

*Primary Examiner*—Cathy Kingdon Worley
(74) *Attorney, Agent, or Firm*—Licata & Tyrrell P.C.

(57) ABSTRACT

The present invention relates to a transformed plant cell expressing β-amyloid gene, which is known as a causal substance of senile dementia in human, a transformed plant and a preparation method of the same, more particularly, to a transformed plant cell expressing tandem repeats of β-amyloid gene, a transformed plant produced by tissue-culturing the above cells and a preparation method of the same. The transformed plant of the present invention expresses multiple β-amyloid protein, so that the plant can be effectively used for the preparation of an oral vaccine composition for the prevention of senile dementia in human.

3 Claims, 8 Drawing Sheets

A
3-β amyloid (450bp)

B
5-β amyloid (750bp)

SEQUENCE LISTING

<160> NUMBER OF SEQ ID NOS: 6

<210> SEQ ID NO 1
<211> LENGTH: 402
<212> TYPE: DNA
<213> ORGANISM: Homo sapien

<400> SEQUENCE: 1

```
atggatgcag aattccgaca tgactcagga tatgaagttc atcatcaaaa attggtgttc        60
tttgcagaag atgtgggttc aaacaaaggt gcaatcattg gactcatggt gggcggtgtt       120
gtcatagcgc agatgctgga tgcagaattc cgacatgact caggatatga agttcatcat       180
caaaaattgg tgttctttgc agaagatgtg ggttcaaaca aaggtgcaat cattggactc       240
atggtgggcg gtgttgtcat agcgcagatg ctggatgcag aattccgaca tgactcagga       300
tatgaagttc atcatcaaaa attggtgttc tttgcagaag atgtgggttc aaacaaaggt       360
gcaatcattg gactcatggt gggcggtgtt gtcatagcgt ga                          402
```

<210> SEQ ID NO 2
<211> LENGTH: 672
<212> TYPE: DNA
<213> ORGANISM: Homo sapien
<220> FEATURE:
<221> NAME/KEY: misc_feature

```
<222> LOCATION: (132)..(132)
<223> OTHER INFORMATION: n is a, c, g, or t
<220> FEATURE:
<221> NAME/KEY: misc_feature
<222> LOCATION: (163)..(163)
<223> OTHER INFORMATION: n is a, c, g, or t
<220> FEATURE:
<221> NAME/KEY: misc_feature
<222> LOCATION: (267)..(267)
<223> OTHER INFORMATION: n is a, c, g, or t
<220> FEATURE:
<221> NAME/KEY: misc_feature
<222> LOCATION: (298)..(298)
<223> OTHER INFORMATION: n is a, c, g, or t
<220> FEATURE:
<221> NAME/KEY: misc_feature
<222> LOCATION: (337)..(337)
<223> OTHER INFORMATION: n is a, c, g, or t
<220> FEATURE:
<221> NAME/KEY: misc_feature
<222> LOCATION: (433)..(433)
<223> OTHER INFORMATION: n is a, c, g, or t
<220> FEATURE:
<221> NAME/KEY: misc_feature
<222> LOCATION: (568)..(568)
<223> OTHER INFORMATION: n is a, c, g, or t

<400> SEQUENCE: 2
atggatgcag aattccgaca tgactcagga tatgaagttc atcatcaaaa attggtgttc      60
tttgcagaag atgtgggttc aaacaaaggt gcaatcattg gactcatggt gggcggtgtt    120
gtcatagcgc anatgctgga tgcagaattc cgacatgact cangatatga agttcatcat    180
caaaaattgg tgttctttgc agaagatgtg ggttcaaaca aggtgcaat  cattggactc    240 atggtgggcg gtgttgtcat agcgcanatg ctggatgcag aattccgaca tgactcanga    300
tatgaagttc atcatcaaaa attggtgttc tttgcanaag atgtgggttc aaacaaaggt    360
gcaatcattg gactcatggt gggcggtgtt gtcatagcgc atatgctgga tgcagaattc    420
cgacatgact cangatatga agttcatcat caaaaattgg tgttctttgc agaagatgtg    480
ggttcaaaca aggggcaat  cattggactc atggtgggcg gggttgtcat agcgcatatg    540
ctggatgcag aattccgaca tgactcanga tatgaagttc atcatcaaaa attggtgttc    600
tttgcagaag atgtgggttc aaacaaaggg gcaatcattg gactcatggt gggcggggtt    660
gtcatagcgt ga                                                        672

<210> SEQ ID NO 3
<211> LENGTH: 21
<212> TYPE: DNA
<213> ORGANISM: Artificial sequence
<220> FEATURE:
<223> OTHER INFORMATION: Synthetic

<400> SEQUENCE: 3
ggatccccca tactttgagt g                                               21

<210> SEQ ID NO 4
<211> LENGTH: 21
<212> TYPE: DNA
<213> ORGANISM: Artificial sequence
<220> FEATURE:
<223> OTHER INFORMATION: Synthetic

<400> SEQUENCE: 4
ggtacccaaa ttttgttggt g                                               21

<210> SEQ ID NO 5
```

```
<211> LENGTH: 27
<212> TYPE: DNA
<213> ORGANISM: Artificial sequence
<220> FEATURE:
<223> OTHER INFORMATION: Synthetic

<400> SEQUENCE: 5
ggtaccggat ccgccatgga tgcagaa                                         27

<210> SEQ ID NO 6
<211> LENGTH: 27
<212> TYPE: DNA
<213> ORGANISM: Artificial sequence
<220> FEATURE:
<223> OTHER INFORMATION: Synthetic

<400> SEQUENCE: 6
gagctcggat ccaactcacg ctatgac                                         27
```

TRANSFORMED PLANT CELL EXPRESSING TANDEM REPEATS OF BETA-AMYLOID GENE AND PLANT PRODUCED BY THE SAME

FIELD OF THE INVENTION

The present invention relates to a transformed plant cell line expressing β-amyloid gene, which is known as a causal substance of Alzheimer type senile dementia in human, a transformed plant and a preparation method of the same, more particularly, to a transformed plant cell expressing tandem repeats (3~5) of β-amyloid genes, a transformed plant produced by tissue-culturing the above cells and a preparation method of the same.

BACKGROUND

WHO pronounced in 1990 that it was its goal to develop a vaccine that was not only safe and stable under heat but also administered orally and supplied widely. The annual vaccine market reached 6 billion dollar scale recently, which was though, continued to be extended to reach 13 billion dollar scale in 2003. A vaccine development system today has some problems such as high price of production facilities and refrigerating equipments necessary for transportation and storage, difficulties in administration of a vaccine, reluctance of people to be injected, etc. So, an alternative vaccine needs to be developed to solve the above problems and especially for the children in underdeveloped countries who have not been favored with preventive inoculation. One of the promising studies to develop an alternative vaccine is a study on plant vaccine for oral administration prepared from transformed crops. An oral plant vaccine has a safety of a recombinant vaccine and easiness in vaccination (oral administration) as well as efficiency. The oral administration of a plant vaccine is just eating a transformed plant inserted with an antigen gene by a plant expression vector, which is as easy as eating food but still can induce immune response.

Korea advances an aging society. Aged men over 65 were 5.7% of total population in 1995 and 7% in 2001, which was a base line for being defined as an aging society by UN. With this tendency, an aged population will reach 15% of total population in 2020. Dementia patients in Korea are estimated to be at least 500,000, and 10,000 to 20,000 new patients are expected to be report annually. According to epidemiological survey, dementia patients are going to be developed by 1 person per 15 families in 2020. Patients with Alzheimer's disease take at least 60% of total dementia patients, which are about 300,000 people. Senile dementia, so called Alzheimer's disease, is a kind of degenerative nervous disease, which progresses for a long while beginning by causing troubles in recognition and going to destroy humanity. Thus, a passive approach to those patients cannot relieve social and economic burdens. An active approach to develop an agent for prevention and treatment of the disease is required.

All the dementia treatment medicines, which have been developed already or are under development, are nothing but symptom relievers, so that they cannot treat a cause of the disease directly but help functioning of cholinergic neurons. From the results of studies on Alzheimer's disease, the cause of the disease is believed to be an accumulation of beta-amyloid, a toxic protein, in brain, resulting in the death of neurons (Bacskai B J et al., 2001, Nature medicine 7:369-372; Schenk D. et al., 1999, Nature 400:173-177). So, one of the most effective ways to prevent and to treat a cause of Alzheimer's disease directly is to develop an agent inhibiting degeneration of nervous system by suppressing the generation of beta-amyloid and toxicity.

Beta-amyloid is a metabolite produced by a protease originated from APP (amyloid precursor protein), type I internal membrane protein, and is composed of 39~43 peptides consisting of domains of a cell and a cell membrane. The beta-amyloid is formed during amyloidogenic metabolism by the action of β-secretase and γ-secretase, sorts of a protease. According to recent studies, a transformed mouse having Alzheimer type dementia caused by the expression of human beta-amyloid showed alleviation of behavior disorder resulted from the elimination of plaques accumulated in brain by the administration of beta-amyloid vaccine (Chen G. et al., 2000, Nature 408: 975-979; Janus C. et al., 2000, Nature 408:979-982; Morgan D. et al., 2000, Nature 408:982-985).

There has been no such attempt, in domestic and in the whole world, to express human beta-amyloid gene in a plant, so that there has been no report yet saying that a transformed plant, in which the gene was expressed, used as a vaccine for the elimination of beta-amyloid plaque.

One of the 4 major principal crops, potatoes have a perfect nutritive composition and has been widely cultivated to feed human through the world except intense cold and heat areas. Therefore, a successful development of a potato vaccine can create a huge steady demand.

In the meantime, tasty tomatoes are also cultivated and consumed world-widely. It is one of their merits to be eaten in the raw, which is one of the best benefits as an oral plant vaccine. Thus, a tomato has already been selected as a target farm product by many researchers. Both potatoes and tomatoes belong to Solanaceae. And it has also been reported that transformation is easy and the expression of an inserted foreign gene is stably completed in them (Chong D. K. X. et al., 1997, Transgenic Res. 6:289-296; Sandhu J. S. et al., 2000, Transgenic Res. 9:127-135).

Thus, in order to develop potatoes and tomatoes expressing beta-amyloid gene for the purpose of using them as oral plant vaccines for the prevention and the treatment of human Alzheimer type dementia, the present inventors inserted multiple beta-amyloid gene into *Agrobacteria* using an expression vector plasmid for transformation containing multiple beta-amyloid gene and cultured thereof together with potato leaves or tomato cotyledon tissues, and the inventors completed the invention by producing potato and tomato plants mass-expressing multiple beta-amyloid gene.

SUMMARY OF THE INVENTION

It is an object of this invention to provide transformed plant cells expressing a toxic protein beta-amyloid, one of the causing substances of Alzheimer type dementia in human.

It is also an object of this invention to provide a transformed plant produced by re-differentiation of the above transformed plant cells by tissue culture.

It is a further object of this invention to provide a preparation method for the transformed plant cells comprising the following steps: i) preparing an expression vector containing tandem repeats of beta-amyloid; ii) inserting the expression vector into *Agrobacterium*; and iii) transforming plant cells by co-culturing with the *Agrobacterium*.

It is also an object of this invention to provide a preparation method for the above transformed plant including re-differentiation of the above transformed plant cells.

It is also an object of this invention to provide an oral vaccine composition for the prevention of dementia containing the above transformed plant as an effective ingredient.

DETAILED DESCRIPTION OF PREFERRED EMBODIMENTS

In order to achieve the above object of the present invention, the present invention provides transformed plant cells expressing a toxic protein beta-amyloid, one of the causing substances of Alzheimer type dementia in human.

The present invention also provides a transformed plant produced by re-differentiation of the above transformed plant cells by tissue culture.

The present invention further provides a preparation method for the transformed plant cells comprising the following steps: i) preparing an expression vector containing tandem repeats of beta-amyloid; ii) inserting the expression vector into *Agrobacterium*; and iii) transforming plant cells by co-culturing with the *Agrobacterium*.

The present invention also provides a preparation method for the above transformed plant including re-differentiation of the above transformed plant cells.

The present invention also provides an oral vaccine composition for the prevention of dementia containing the above transformed plant as an effective ingredient.

"In vitro culture" in the present invention means culturing in a sterilized incubator, "small tuber" means a in vitro tuber of a potato reduced to the size of a soybean from a tuber, and "explant" means transferring a plant in an in vitro culture condition or putting therein.

Hereinafter, the present invention is described in detail.

The present invention provides transformed plant cells expressing tandem repeats of beta-amyloid genes, a kind of toxic protein inducing Alzheimer type dementia in human.

It is preferred to select a plant for the invention from those belonging to Solanaceae, for example, potatoes and tomatoes, and is also preferred to transform the plant by the insertion of *Agrobacterium*. Although the kind of *Agrobacterium* is not limited in use, *Agrobacterium tumefaciens* LBA4404 is preferred. An expression vector is not limited to a specific one, either, but an expression plasmid comprising kanamycin-resistant gene, CaMV35 promoter and patatin promoter of a potato is preferred (see FIG. 2) as an expression vector for the insertion of multiple beta-amyloid gene into the *Agrobacterium*.

In the preferred embodiment of the present invention, in order to produce a potato and a tomato plants expressing multiple beta-amyloid, a plant transfecting expression plasmid containing multiple beta-amyloid gene was used to insert multiple beta-amyloid gene into *Agrobacteria*. The bacteria was co-cultured with potato plant leaf sections which were under in vitro culture and cotyledon sections of tomato seedlings germinated a week earlier, resulting in the preparation of a transformed plant. For the co-culturing with plant tissues, leaf sections were wounded by cut. Callus was formed in the wounded area where organs were differentiated, leading to the re-differentiation of a plant (see FIG. 3). Each re-differentiated transformed plant was bred by an appropriate tissue culture method. As for a potato, in particular, the formation of small tuber was induced massively in a culture medium supplemented with over 9% sucrose, which was comparatively high sugar concentration. All the expression vectors for the transformation of plants and *Agrobacterium* strains including any of those expression vectors can be included in the criteria of the present invention, and the mentioned expression vectors and *Agrobacterium* strain are available for the transformation of many other plants in addition to potatoes and tomatoes. That is, there is no special limitation in plant cells expressing multiple beta-amyloid. Just edible plants are preferred, and especially farm products that can be raised and met everywhere in the country and are in plentiful supply, like potatoes, tomatoes and lettuce, are more preferred.

In the present invention, beta-amyloid cDNA was obtained by PCR using both-directed primer of beta-amyloid consisting of 40~42 peptides which was separated from APP (amyloid precursor protein) gene taken from brain of a dementia patient. It is not easy to detect the expression of a 120 bp long single beta-amyloid gene in a plant. Therefore, the present inventors linked 3~5 single beta-amyloid genes in series, in order to increase the expression of beta-amyloid in a plant. After inserting the multiple beta-amyloid genes into a cloning vector, base sequences were investigated, resulting in the confirmation that whole base sequence was preserved even after the link of 3~5 beta-amyloid genes (see FIG. 1).

The present inventors deposited an *Agrobacterium tumefaciens* LBA4404 strain transfected with an expression vector containing the multiple beta-amyloid genes at Korean Collection for Type Culture (KCTC) of Korea Institute of Bioscience and Biotechnology (KRIBB), on Mar. 10, 2003 (Accession No: KCTC 10444BP).

The present invention also provides a transformed plant prepared by re-differentiating the above transformed plant cells by tissue culture.

The plant herein is preferred to be potatoes or tomatoes, and re-differentiation method is not limited to a specific one. In this invention, though, it is preferred to form callus first by tissue culture and then organs were induced.

A potato plant could be transformed by co-culturing *Agrobacterium* containing multiple beta-amyloid genes together with sections of potato and tomato plant cells under tissue culturing. The transformed plant can express multiple beta-amyloid during the process of re-differentiation. The transformed potato produced in the embodiment of the present invention was investigated by western blotting and ELISA, resulting in the confirmation that multiple beta-amyloid genes were expressed (see FIG. 6 and FIG. 7). Each extract of a transformed potato and a transformed tomato was oral-administered to a test mouse, showing a rapid increase of an antibody against beta-amyloid (see FIG. 8). Therefore, the transformed potato and the transformed tomato developed by the present inventors can be used as a composition for a preventive vaccine for dementia.

The present invention further provides a preparation method for the transformed plant cells comprising the following steps: i) preparing an expression vector containing tandem repeats of beta-amyloid; ii) inserting the expression vector into *Agrobacterium*; and iii) transforming plant cells by co-culturing with the *Agrobacterium*.

In the preferred embodiment of the present invention, tandem repeats of beta-amyloid genes were inserted in a potato and in a tomato to induce their expression therein. Particularly, tandem repeats of beta-amyloid genes, in which 3~5 single beta-amyloid genes were linked, were inserted into an *Agrobacterium tumefaciens* strain by using an expression vector (see FIG. 2) consisting of CaMV35S (Cauliflower Mosaic Virus 35S) promoter or patatin promoter of a potato. The strain transfected with the above expression vector was used to transform potato and tomato cells.

The preparation steps of the above strain transfected with an expression vector were more precisely explained hereinafter. 3~5 beta-amyloid genes were linked, followed by cloning. The genes were inserted into pMBPnAβ vector including kanamycin-resistant gene by taking advantage of CaMV35S promoter or into pATnAβ vector being expressed specifically in a tuber of a potato by taking advantage of patatin protein promoter. Then, the vectors were respectively inserted into an

*Agrobacterium tumefaciens* strain LBA4404. At that time, PCR was performed to confirm if whole sequences of multiple beta-amyloid genes were preserved in the above expression vector. At last, transformed potato and tomato cells were prepared by co-culturing the strain together with potato and tomato cells.

The present invention also provides a preparation method of the above transformed plant including the step of re-differentiating the transformed plant cells above.

In the preferred embodiment of the present invention, in addition to the preparation of the transformed potato and tomato cells, transformed potato and tomato plants were produced by co-culturing the above strain with sections of potato and tomato plant leaves.

Precisely, young leaves under a week from coming out were taken from a stem of a potato plant that was kept under in vitro culture and ready to be inserted in a potato plant anytime. After making many cuts on the young leaves, the leaves were sunk in *Agrobacteria* culture solution for co-culturing, which were transferred to a callus-inducing medium to induce the formation of callus. As for using a tomato, cotyledon less than a week from germination was cut, which was sunk in *Agrobacteria* culture solution for co-culturing and then transferred to a callus-inducing medium to induce the formation of callus.

Small plants were obtained from the transformed potato callus and the tomato callus, which were proliferated for about 4 weeks. Then, a potato was further cultured in a sugar medium having over 9% sugar concentration, resulting in 1 g of small tuber. In the meantime, a tomato was transplanted in a green house for growing up.

Multiple beta-amyloid genes inserted in the transformed potatoes and tomatoes were confirmed by PCR (polymerase chain reaction) (see FIG. 4). Besides, a whole RNA was extracted from the transformed potato to investigate the expression of beta-amyloid specific transcript by northern blotting (see FIG. 5). The expression of multiple beta-amyloid proteins in plants was investigated by Western blotting and ELISA. As a result, the expression of the protein that cannot be detected in normal plants generally was seen in a plant having the link of patatin promoter and 5-beta-amyloid, in a transformed potato having the link of CaMV35S promoter and 5-beta-amyloid and in a transformed tomato having the link of CaMV35S promoter and 3-beta-amyloid, all suggesting the introduction of multiple beta-amyloid genes.

The present invention also provides an oral vaccine composition for the prevention of dementia containing the above transformed plant as an effective ingredient.

Herein, a plant is preferably a potato or a tomato, and the above transformed plant can be used either as it is or in the form of dried powder or together with other food or edible ingredients, following general administration methods. An effective dosage of a plant can be determined according to a purpose of use (prevention, treatment or improvement of health), but generally, there is no limitation in use of an effective ingredient, the plant, since the plant has been proved to be safe.

There is no boundary for the kinds of food that can contain the above composition, for example, meat, sausage, bread, chocolate, candies, snacks, cookies, pizza, ramyun, noodles, gums, dairy products including ice creams, soups, beverages, tea, drinks, alcoholic beverages, vitamins, etc, but not always limited thereto.

BRIEF DESCRIPTION OF THE DRAWINGS

The application of the preferred embodiments of the present invention is best understood with reference to the accompanying drawings, wherein:

FIG. 5 is a set of photographs showing the expression of mRNA confirmed by Northern blotting, which was investigated to examine transcription of multiple beta-amyloid genes in transformed plants selected by PCR confirmation, (A) NC; Normal tomato plant which was not transfected, Lane 2-8; Transformed tomato plants (different clones) in which pMBP3Aβ plasmid was inserted respectively, (B) NC; Normal potato plant which was not transfected, Lane 1-3; Transformed potato plants (different clones) in which pMBP3Aβ plasmid was inserted respectively, (C) N; Normal potato plant which was not transfected, Lane 1-6; Transformed potato plants (different clones) in which pPAT5Aβ plasmid was inserted respectively.

EXAMPLES

Figure 1:
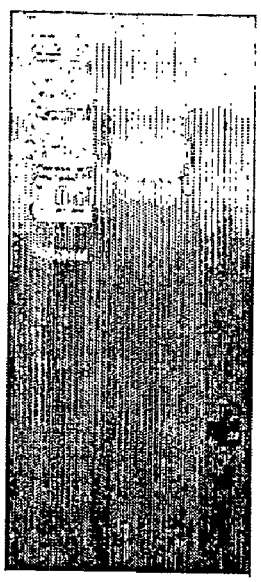
FIG. 1 is a set of electrophoresis photographs showing the sizes of 3-beta-amyloid and 5-beta-amyloid genes that were inserted in a cloning vector of the present invention.
Figure 1:

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Cultivation of Plants

<1-1> Cultivation of a Potato

For a potato plant of the present invention, *Solanum tuberosum* cv. Desiree, a potato race that was proved to be bacteria or virus free, was germinated. Then, it was cut into as small sections as possible (each has to include growing point). The surface of each section was sterilized by 70% ethanol, followed by tissue culture. The sterilized potatoes were washed with distilled water, followed by sterilization again for 10 minutes in 10% sodium hypochloride solution. The potatoes were washed three times with distilled water. After removing moisture, the potatoes were placed in a basal medium prepared by adding sucrose by 3% to MS salt (Duchefa co., Cat. No. M0221) to induce growth of a stem. As a stem was actively growing in an incubator, sub-culture was carried out every 2 weeks to keep tissue culture of a potato plant. A medium prepared by adding sucrose (90 g/L) to MS basal medium was used for the formation of small tuber, and potato plant tissues were cultured at 17° C. with 8-hour light cycle. For the formation of small tuber in vitro, lower part of a potato stem which was grown for 2~3 weeks under the above culture condition was explanted. Two weeks after being explantation, storage stem became expanded. 8 weeks later, more than 1 g of mature small tuber could be obtained.

A young leaf grown up for about 1 week was cut and used for co-culturing with *Agrobacteria* for the transformation. A medium for callus formation was prepared by adding 3% sucrose, 8% agarose and 2.0 mg/L 2,4-D (2,4-dichlorophenoxy acetic acid) (Sigma co., Cat No. D08407) to MS medium, in which pH was adjusted to 5.8. The transformed leaf sections were cultured in a callus-inducing medium containing 2,4-D, which was then transferred to a re-differentiating medium containing 0.01 mg/L NAA (Sigma co., Cat No. N-0375), 0.1 mg/L GA3 (Sigma co., Cat No. G7645) and 2.0 mg/L Zeatin (Duchefa co., Cat No. Z0917). A week after the transfer, callus was formed around the wounded area of a leaf section. And from 4 weeks after the transfer, a small plant was appeared. The small plant was cultured until separation was possible. Then, the small plant was transferred to MS basal medium. While the plant was proliferated by the same procedure for a normal plant, the formation of small tuber was induced.

<1-2> Cultivation of a Tomato

Seeds of a Dotaerang, a tomato race for cultivation, were treated with 70% ethanol lightly for surface sterilization. After washing the seeds with distilled water, they were sterilized in 10% sodium hypochloride solution for 10 minutes. Then, the seeds were washed three times with distilled water. After removing moisture, the seeds were explanted in a basal medium prepared by adding sucrose by 3% to MS salt to induce germination. A week after the germination, cotyledons were coming out. The cotyledon was wounded by cut and used for co-culture with *Agrobacteria* for transformation. The medium used to induce callus formation was prepared by adding. 3% sucrose, 8% agarose and 1.0 mg/L Zeatin to MS medium, in which pH was adjusted to 5.8. The prepared cotyledon sections were cultured in the same callus inducing medium as used in Example <1-1>, then, transferred to a re-differentiating medium containing 2.0 mg/L Zeatin. A week after the transfer, callus was formed around the wounded area of a leaf section. And from 4 weeks after the transfer, a small plant was appeared.

Example 2

Figure 2:
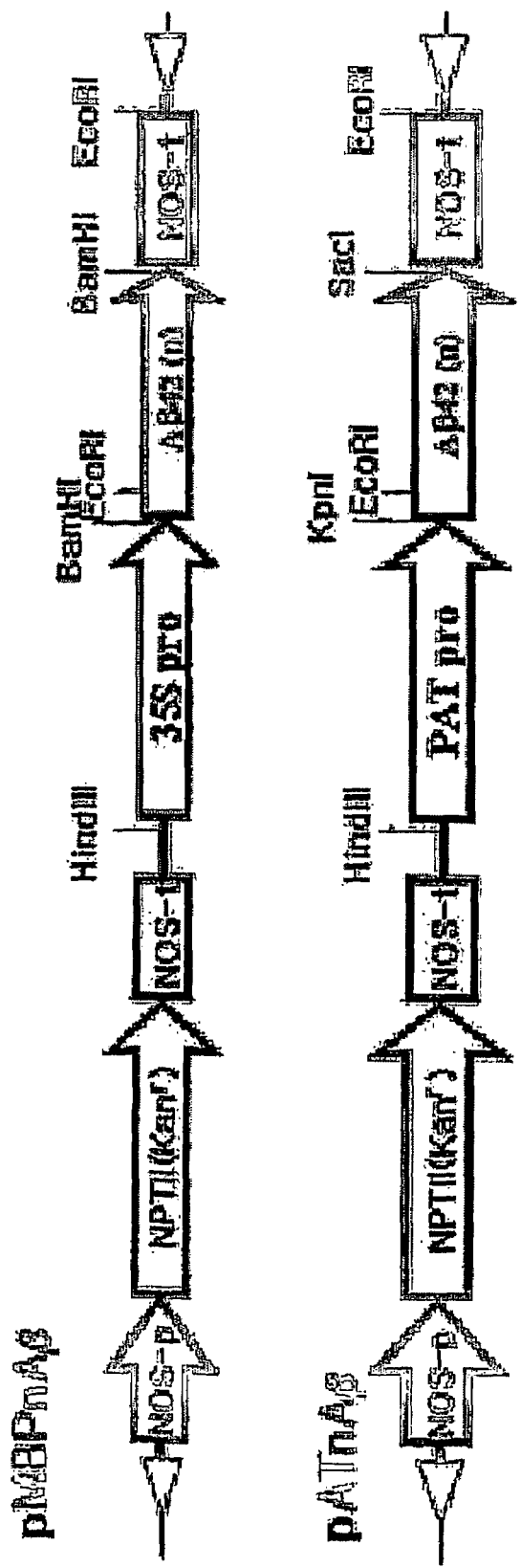
FIG. 2 is a schematic diagram showing the transforming vectors 'pMBPnAβ' and 'pATnAβ' prepared by inserting 3-beta-amyloid gene and 5-beta-amyloid gene into plant expression vectors 'pMBP' and 'pAT.

Insertion of Multiple Beta-amyloid Genes into Potato and Tomato Leaf Sections <2-1> Construction of Plasmids for Plant Transformation In order to transform a potato and a tomato, the present inventors prepared plasmids pMBP3Aβ PMBP5Aβ and pAT5Aβ (FIG. 2). Those vectors were constructed by linking 3 connections (3-beta-amyloid) or 5 connections (5-beta-amyloid) of human beta-amyloid genes to CaMV35S promoter (pMBP3Aβ, pMBP5Aβ) and patatin promoter, a potato tuber specific expression promoter (pAT5Aβ), respectively. In this invention, pMBP1 vector, which was a vector for plant transformation prepared by removing GUS gene from pBI121 vector (Clontech co., Cat. No. 6018-1), was digested with BamH I. Then, 3-beta-amyloid gene represented by SEQ. ID. No 1 and 5-beta-amyloid gene represented by SEQ. ID. No 2 were inserted in between CaMV35S promoter and nos terminator. For the patatin promoter, primers represented by SEQ. ID. No 3 and No 4 were prepared based on base sequence reported by Liu et al. (Liu et al., Plant Mol Biol 17: 1139-1154, 1991), and PCR was performed with the primers. CaMV35S promoter of pBI121 vector was substituted with the patatin promoter amplified by PCR, resulting in the preparation of a plant transforming vector 'pATGUS'. GUS gene of the pATGUS vector was cut by restriction enzymes, Kpn I and Sac I, where 5-beta-amyloid gene represented by SEQ. ID. No 2 was inserted, leading to the construction of pAT5Aβ vector. Those vectors include nptII, a kanamycin-resistant gene, as a selection marker. Each plasmid DNA of the vectors prepared above was inserted into *Agrobacterium tumefaciens* LBA4404 (Gibco BRL co., Cat. no. 18313-015), which was used for plant transformation.

<2-2> Transformation of Plants with an *Agrobacterium tumefaciens* Strain

In order to insert multiple beta-amyloid genes in potato and tomato leaf sections, potato leaves cultured less than 7 days and about 100 cotyledons of a tomato coming out around 7 days ago were selected and sunk in *Agrobacterium tumefaciens* LBA4404 (Gibco BRL, Cat. No. 18313-015) culture solution for 10 minutes. Then, moisture was completely removed on a sterilized paper. Potato leaf sections were explanted in a co-culture medium containing 2.0 mg/L 2,4-D and so were tomato leaf sections in a co-culture medium containing 1.0 mg/L Zeatin. They were cultured for 2 days. The procedures were to induce callus around wounded areas in the leaf sections. At that time, antibiotics like kanamycin had to be avoid to increase the chance of insertion of *Agrobacteria* into a plant gene. As callus was about to be form in the wounded area, potato leaf sections were transferred to MS medium (Duchefa co., Cat. No. M0221) containing 0.01 mg/L NAA (α-Naphthalene Acetic Acid), 0.1 mg/L GA3 (gibberellin) and 2.0 mg/L Zeatin, in order to induce re-differentiation of a small plant. Likewise, tomato cotyledon sections were transferred to MS medium (Duchefa co., Cat. No. M0221) containing 2.0 mg/L Zeatin. Selection pressure was given by adding 100 mg/L kanamycin in order for only transformed plants to be re-differentiated. 1,000 mg/L carbenicillin (Duchefa co., C0109) was added into a culture medium to remove excessive *Agrobacteria* remaining on the sections without being inserted. During the re-differentiation of a transformed small plant, a culture medium was replaced by fresh one every 2 weeks.

Figure 3:
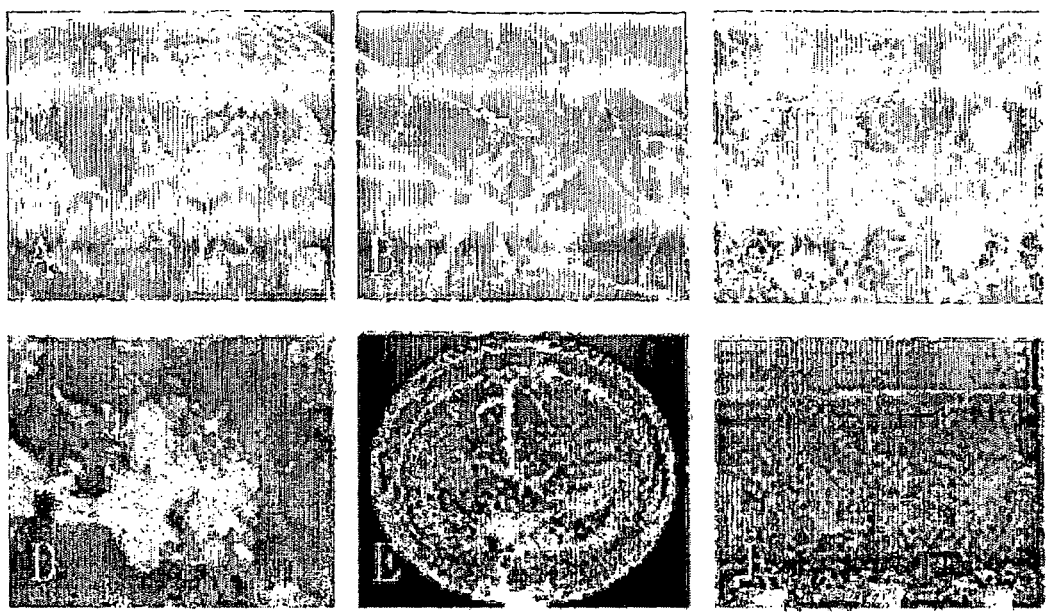
FIG. 3 is a set of photographs showing the transformed potato plant which was growing in a growth medium by being induced in callus after inoculation of *Agrobacteria*, and the formation of its small tuber (A~C), and the callus inducing process in tomato cotyledon sections as well as the culture of transformed plants (D~F), A; Small potato plants under re-differentiation in a formed callus, B; Re-differentiated small potato plants which were growing in an in vitro incubator, C; Potatoes, in which the formation of small tuber was going on, D; Small tomato plants under re-differentiation in a formed callus E; Re-differentiated small tomato plant which was growing in an in vitro incubator F; Tomato plants growing in a green house, which was transplanted later into a flowerpot from an in vitro incubator

The transformed leaf sections were sub-cultured in the same selection media at 2 weeks interval. 8 weeks later, about 50 small individual plants were obtained. From comparing a plant raised in vitro with a normal plant, any abnormal shape was not observed. The growth of a potato was also observed after transplantation in a medium for the formation of small tuber, which seemed to be very normal and even normal potato small tuber was obtained. The growth of a tomato transplanted from in vitro to a flowerpot was observed, too, proving that a tomato was grown up as a normal individual (FIG. 3). From the above results, the insertion of multiple beta-amyloid genes into potato or tomato plants was proved to be safe and stable not to affect normal growth of a plant.

Example 3

Confirmation of Insertion of Multiple Beta-amyloid Genes by PCR

PCR (polymerase chain reaction) was performed to confirm the insertion of multiple beta-amyloid genes into plants. Particularly, chromosomal DNA was extracted from sections of a small plant leaves selected from the medium containing kanamycin. The chromosomal DNA was used as a template, and a forward primer represented by SEQ. ID. No 5 and a backward primer represented by SEQ. ID. No 6 were used for the PCR amplification. The prepared PCR mixture was denatured at 94° C. for 2 minutes (precycling reaction), followed by 20 cycles of denaturation at 94° C. for 45 seconds, annealing at 65° C. for 1 minute, polymerization at 72° C. for 1 minute, and final extension at 72° C. for 5 minutes. After PCR, the PCR product was analyzed by agarose gel electrophoresis.

Figure 4:
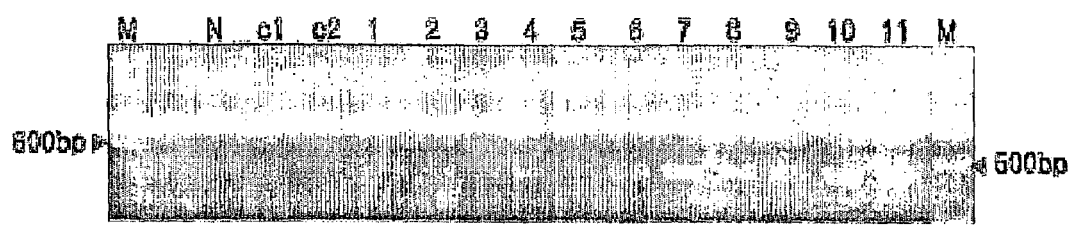
FIG. 4 is a set of electrophoresis photographs showing the beta-amyloid genes included in re-differentiated plants of a potato or a tomato transfected with pMBP3Aβ vector (A), with pMBP5Aβ vector (B) and with pAT5A vector (C), which were confirmed by PCR, (A) M; 100 bp size DNA marker, N; Negative control, C1, C2; Normal tomato plant which was not transfected, Lane 1-11; Transformed tomato plants (different clones) in which pMBP3Aβ plasmid was inserted respectively, (B) M; 100 bp size DNA marker, N; Normal potato plant which was not transfected, Lane 1-5; Transformed potato plants (different clones) in which pMBP3Aβ plasmid was inserted respectively, (C) M; 100 bp size DNA marker, N; Normal potato plant which was not transfected, Lane 1-14; Transformed potato plants (different clones) in which pPAT5Aβ plasmid was inserted respectively.
Figure 4:
Figure 4:
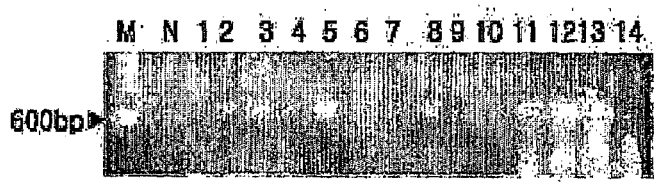

As a result, a 0.75 kb 5-beta-amyloid DNA band and a 0.4 kb 3-beta-amyloid DNA band were confirmed (FIG. 1 and FIG. 4). From the above results, NPTII gene, a selection marker was confirmed to be included in transformed potato and tomato plants, which was, though indirectly, confirmed by observation on an antibiotics-selection medium. And multiple beta-amyloid genes were also confirmed to be included in potatoes and tomatoes.

Example 4

Figure 5:
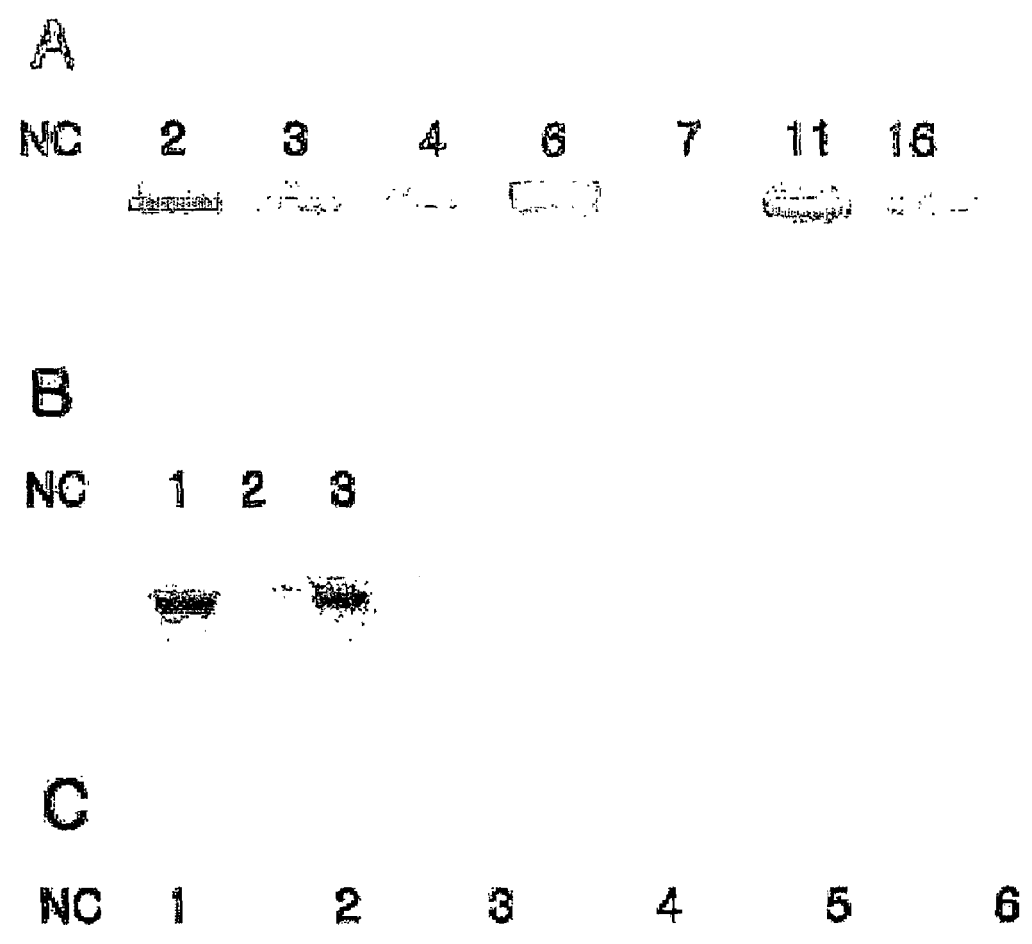

Investigation of Transcripts of Multiple Beta-amyloid Included in Transformed Potato and Tomato Plants The expressions of RNA in transformed potato and tomato plants were investigated for the best selection. 1 g of leaves and shoots of a transformed potato containing pMBP5Aβ was taken to -extract a whole RNA. 1 g of generated small tuber of a transformed potato containing pAT5Aβ was also taken to extract a whole RNA. 1 g of leaves, and shoots of a transformed tomato containing pMBP3Aβ was taken to investigate RNA. Purified RNA was quantified. Then, 30 μg of RNA was electrophoresed in agarose gel containing 19.8% formaldehyde. RNA in the gel was transferred to a nylon membrane with no special pre-treatment. In order to fix the transferred RNA on the nylon membrane, UV-irradiation was performed twice by 1200×μJ/cm². In order to observe a beta-amyloid specific RNA band with the naked eye in the nylon membrane, a probe on which DIG marker was attached was fixed on the nylon membrane at 50° C. for 16 hours. A diagnostic kit (Boeringer Mannheim co., cat no. 1093 657) available for detecting DIG was used to observe beta-amyloid specific RNA band. As a result, beta-amyloid specific transcripts were confirmed in 5 transformed potatoes and 7 transformed tomatoes (FIG. 5).

Example 5

Analysis on the Expression of Multiple Beta-amyloid Proteins

Figure 6:
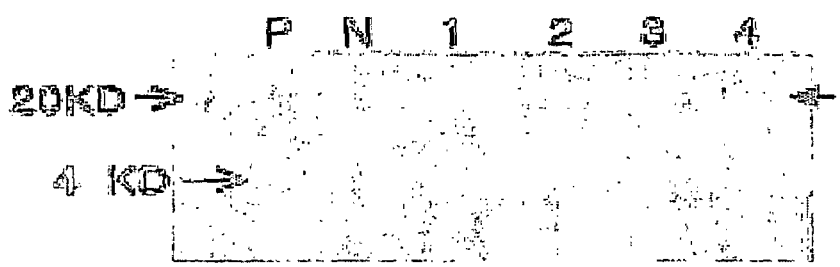
FIG. 6 is a set of electrophoresis photographs each showing tomato leaves expressing pMBP3Aβ (A), transformed potato leaves expressing pMBP5Aβ (B), and the expression of beta-amyloid protein in a transformed potato small tuber expressing pAT5Aβ (C), confirmed by Western blotting using monoclonal antibody 4G8, (A) P; Beta-amyloid peptide used as a positive control,
NC; Normal tomato plant which was not transfected,
Lane 1-6; Transformed tomato plants (different clones) in which pMBP3Aβ plasmid was inserted respectively,
(B) P; Beta-amyloid peptide used as a positive control,
NC; Normal potato plant which was not transfected,
Lane 1-3; Transformed potato plants (different clones) in which pMBP5Aβ plasmid was inserted respectively,
(C) P; Beta-amyloid peptide used as a positive control,
N; Normal potato plant which was not transfected,
Lane 1-5; Transformed potato plants (different clones) in which pPAT5Aβ plasmid was inserted respectively.
Figure 6:
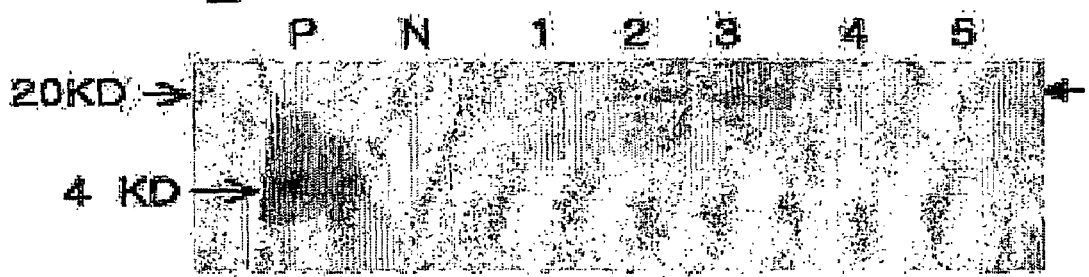
Figure 6:
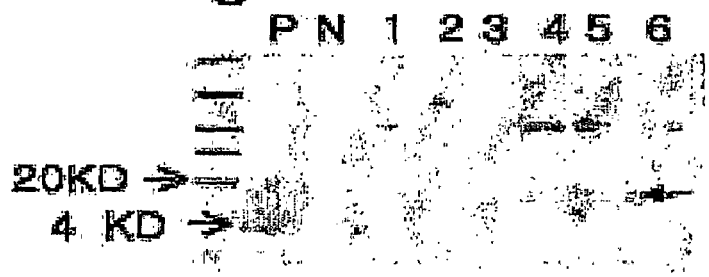

Multiple beta-amyloid proteins expressed in transformed potato and tomato plants were analyzed by Western blotting (FIG. 6). The proteins were extracted from leaves of 4 individual transformed potato plants expressing pMBP5Aβ and from 5 small tubers of individual transformed potato plants expressing pAT5Aβ. Also, the proteins were extracted from leaves of 6 individual transformed tomato plants expressing pMBP3Aβ. An extraction buffer was prepared by mixing PBS buffer (pH 7.2), 10 mM EDTA, 1 mM proteinase inhibitor cocktail (Roche co., cat no. 1873580), 0.1% triton X-100 and 5 mM β-mercaptoethanol. The extraction buffer was added by the half volume of total sample weight. The extract temperature was set at ±4° C. and the extraction was done fast.

As a result, a very clear 20 kDa specific protein band was confirmed in 3 transformed individual potatoes expressing pMBP5Aβ (pMBP5Aβ-1, 5 and 6) and in 2 transformed individual potatoes expressing pAT5Aβ (pAT5Aβ-1 and 3). A 12 kDa specific protein band was also observed in 4 transformed individual tomatoes expressing pMBP3Aβ (pMBP3Aβ-6, 8, 13 and 23). The above beta-amyloid specific bands were not observed in a control group (normal plants), and a beta-amyloid protein having a peptide sequence represented by SEQ. ID. No 6 and comprised 42 peptides made a clear band at 4 kDa, suggesting that all the experiments were correctly done.

Enzyme-linked Immunosorbent assay (ELISA) was performed with proteins of transformed potato and tomato plants extracted by the same method above to confirm antigenicity of the plant expressing the proteins. pMBP3Aβ-6 among tomato plants and pMBP5Aβ-1 and pAT5Aβ-1 of potato plants were investigated since they showed the highest expression of the protein.

Figure 7:
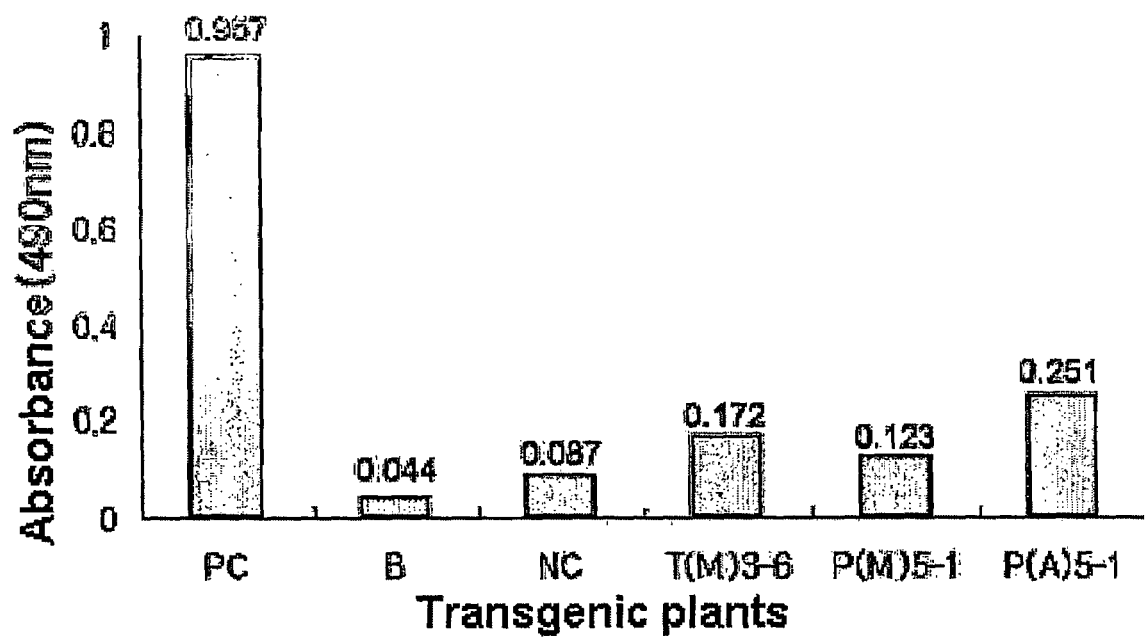
FIG. 7 is a graph showing the results of ELISA performed to examine antigenicity of transformed potato and tomato plants in which multiple beta-amyloid proteins were expressed for sure, confirmed by Western blotting, PC; Beta-amyloid peptide used as a positive control,
B; Reaction buffer used as a negative control,
NC; Normal potato plant which was not transfected,
T(M)3-6; Transformed tomato plant #6 in which pMBP3Aβ plasmid was inserted,
T(M)5-1; Transformed potato plant #1 in which pMBP5Aβ plasmid was inserted,
T(A)5-1; Transformed potato plant #1 in which pPAT5Aβ plasmid was inserted.

As a result, optical density of beta-amyloid peptide of a control was 0.967 and optical density of a normal control plant, which was not transformed, was 0.087. Optical densities of tomato pMBP3Aβ-6, potato pMBP5Aβ-1, and potato pAT5Aβ-1 were 0.172, 0.120 and 0.251, respectively. The experiments were repeated to make sure the results, by which optical densities of those transformed plants above were proved to be 2-3 fold higher than that of a control plant (FIG. 7).

Example 6

Inducement of Immune Response in Test Mice

The protein was extracted from 5 g of leaves of potato transformant pMBP5Aβ-1 and tomato transformant pMBP3Aβ-6, which showed the highest expression of the protein through ELISA analysis. The extract was freeze-dried, resulting in 0.5 ml of concentrate. The protein in a normal potato was used as a control. Each experimental group was given 10 BALB/c mice, and an oral administration was carried out at a week interval for 3 weeks. Serum was taken every week to check an antibody formation. On $4^{th}$ week, oral boosting with original antigen was performed. ELISA was performed to investigate an antibody formation.

Figure 8:
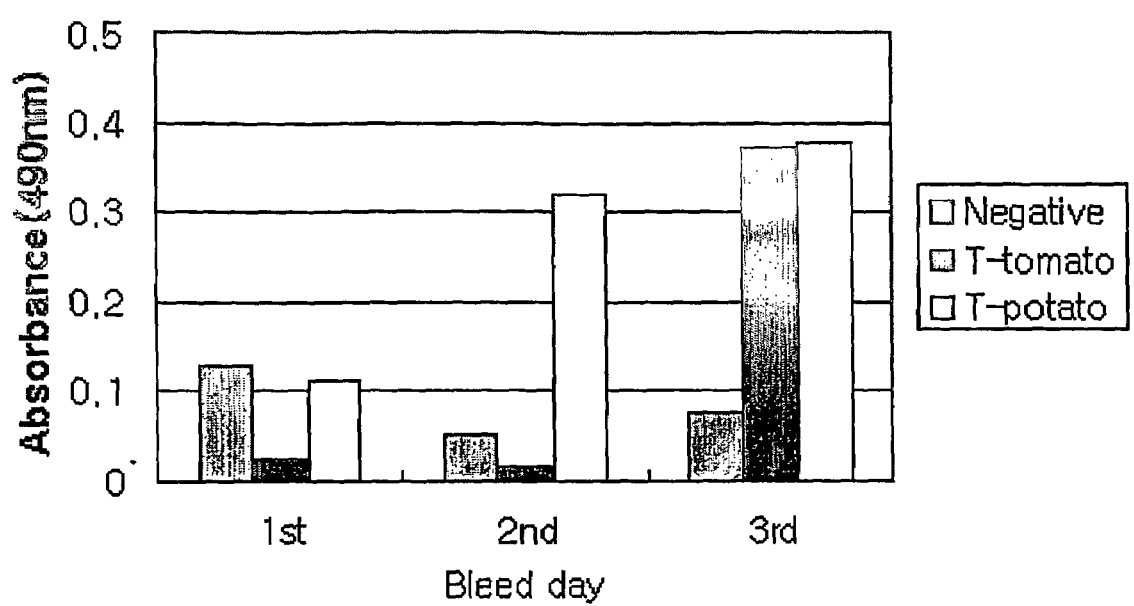
FIG. 8 is a graph showing the results of ELISA quantifying an antibody against beta-amyloid in sera of test mice after the oral administration of each extract of transformed potato and tomato plants expressing multiple beta-amyloid proteins and of a control potato plant.

As a result, an antibody formation in a control, in which a normal plant was administered, became lower than before administration. On the contrary, antibody formations in transformed potatoes and tomatoes containing beta-amyloid protein were rapidly increased (FIG. 8).

Therefore, it has been confirmed that the transformed plants of the invention can be effectively used for the development of a preventive vaccine for Alzheimer type dementia.

INDUSTRIAL APPLICABILITY

As explained hereinbefore, the present inventors have inserted tandem repeats of genes of beta-amyloid, a toxic protein that is a causing substance for Alzheimer type dementia in human, into potato and tomato plants, then developed a transformed plant over-expressing the protein. The development of this plant can greatly contribute to the development of an oral plant vaccine for preventing and treating dementia since potatoes and tomatoes, which are found everywhere and in plentiful supply, can be successfully introduced to the development of a transformed plant available for a vaccine by the present inventors.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. A transformed plant produced by re-differentiation of a transformed plant cell expressing a tandem repeat of beta-amyloid, wherein the transformed plant cell is prepared by introducing a vector containing a tandem repeat of beta-amyloid cDNA consisting of 3 beta-amyloid units which expresses a protein consisting of beta-amyloid protein and wherein the re-differentiation is performed by forming callus by tissue culture from the transformed plant cell and inducing organs.

2. The transformed plant of claim 1, wherein the plant is a potato or a tomato.

3. The transformed plant of claim 1, wherein the transformed plant induces an immune response of a subject when the plant is administered orally to the subject.

* * * * *